United States Patent

Orlowski et al.

[11] Patent Number: 5,925,689
[45] Date of Patent: Jul. 20, 1999

[54] ADHESIVE COATINGS CURABLE BY LIGHT

[75] Inventors: Jan A. Orlowski, Altadene; David V. Butler, West Covina; Jeffrey R. H. MacDonald, Pomona, all of Calif.

[73] Assignee: Scientific Pharmaceuticals, Inc., Pomona, Calif.

[21] Appl. No.: 08/880,106

[22] Filed: Jun. 20, 1997

[51] Int. Cl.$^6$ .................................. C08F 2/46; C08K 2/46
[52] U.S. Cl. ..................... 522/182; 522/120; 522/121; 522/83; 522/918; 522/37; 522/48; 522/141; 522/142
[58] Field of Search .................... 522/182, 83, 141, 522/142, 120, 121, 14, 918; 523/115, 116; 204/159.19

[56] References Cited

U.S. PATENT DOCUMENTS

| | | | |
|---|---|---|---|
| 4,150,485 | 4/1979 | Lee et al. | 35/15 |
| 4,234,399 | 11/1980 | McDowell et al. | 204/159.19 |
| 4,407,984 | 10/1983 | Ratcliffe et al. | 523/115 |
| 4,457,818 | 7/1984 | Denyer et al. | 204/159.19 |
| 4,602,076 | 7/1986 | Ratcliffe et al. | 522/7 |
| 4,648,845 | 3/1987 | Orlowski et al. | 433/217.1 |
| 4,689,015 | 8/1987 | Denyer et al. | 433/217.1 |
| 4,705,836 | 11/1987 | Ohtsuka et al. | 526/318.1 |
| 4,820,744 | 4/1989 | Kubota et al. | 522/13 |
| 4,938,831 | 7/1990 | Wolf, Jr. | 156/275 |
| 5,006,340 | 4/1991 | Atsuta et al. | 424/405 |
| 5,030,392 | 7/1991 | Grossman et al. | 264/16 |
| 5,043,361 | 8/1991 | Kubota et al. | 522/10 |
| 5,063,257 | 11/1991 | Akahane et al. | 523/116 |
| 5,380,772 | 1/1995 | Hasegawa et al. | 522/14 |
| 5,433,941 | 7/1995 | Patel | 424/50 |
| 5,449,703 | 9/1995 | Mitra et al. | 522/57 |
| 5,489,625 | 2/1996 | Moriwaki et al. | 523/118 |
| 5,607,985 | 3/1997 | Masuhara et al. | 522/25 |
| 5,667,541 | 9/1997 | Klun et al. | 51/298 |
| 5,773,489 | 6/1998 | Sato | 523/115 |

*Primary Examiner*—James J. Seidleck
*Assistant Examiner*—Sanza McClendon
*Attorney, Agent, or Firm*—Evan M. Kent; Stewart L. Gitler

[57] ABSTRACT

Adhesive coatings designed primarily for protecting, restoring, repairing, or modifying surfaces of, objects made of polymeric materials. Such coatings are particularly useful in application over worn, cracked, discolored, or otherwise defective objects made of polyacrylic, polystyrene, and polycarbonate resins. The adhesives of this invention are basically comprised of blends containing a substantial concentration of tetrahydrofurfuryl methacrylate and/or furfuryl methacrylate.

6 Claims, No Drawings

_5,925,689_

ADHESIVE COATINGS CURABLE BY LIGHT

BACKGROUND OF THE INVENTION

1. Field of the Invention

This invention relates to adhesive coatings designed primarily for protecting, restoring, repairing, or modifying surfaces of objects made of polymeric materials. They are particularly useful in application over worn, cracked, discolored, or otherwise defective objects made of polyacrylic, polystyrene, and polycarbonate resins.

2. Brief Description of the Prior Art

Acrylic coatings, also frequently called sealers, varnishes, or glazes, are commonly used in many industries. The reason for their application includes protection, restoration, surface smoothing, improving surface characteristics, and enhancing aesthetics of objects made of plastics, metal, wood, ceramics, and paper, as well as human and animal tissues.

Such coatings found, among others, many diversified uses in the dental field as protective sealants over tooth enamel and dentin, for repairing and/or reconditioning of dentures and orthodontic plates, as glazes over composite restorations, for sealing margins in restored cavities, for enhancing bonding and/or adhesion between dental restorations or cements and the tooth structures, and for restoring and/or repairing worn or damaged dental prostheses.

The coating used for such applications may be divided into two basic groups which differ in the way the transfer from the liquid (monomer) state to the solid (polymer) state is accomplished.

The first group consists of two parts, blending of which causes the material to cure (harden). Such parts may be identical, substantially similar, or different in their basic chemical composition. One such part contains a polymerization activator (accelerator) and the other contains a polymerization initiator (usually, although incorrectly, called a catalyst). The most commonly used activators are comprised of tertiary aromatic amines, examples of which are N,N-dimethyl-p-toluidine or N,N-bis(2-hydroxyethylo)-p-toluidine. The most frequently used polymerization initiator is benzoyl peroxide.

The second group of coatings represent materials curable by exposure to electromagnetic energy. UV or visible light are the most convenient forms of such energy. For applications involving human bodies, particularly in dentistry, materials designed for cure with light sources operating in the visible range are preferred due to concern for biological safety and because they offer better curing characteristics and more convenient handling.

Light-cured materials represent a one-component system which offers advantages over its two-component counterpart because of its simplicity and excellent reproduction of properties of the cured material. Light-cured materials are also less sensitive to adverse storage conditions, offering a long shelf-life with no need for refrigeration.

For light-induced polymerization to occur in a clinically or commercially acceptable time frame (a few seconds to a maximum of a few minutes), the sealant must be formulated using highly reactive acrylic monomers, and polymerization activators/initiators must be present at sufficient concentrations. The polymerization-initiating systems most commonly recognized as effective and biologically safe include α,β-diketones, representative of which are camphoroquinone and benzil, and various tertiary aliphatic amines, for example, diethylo (or dimethylo) ethyl methacrylate and ethyl diethanolamine.

Prior art light-cured coatings had, however, limitations with respect to their scope of applications, especially in uses requiring adhesion to certain polymeric materials. Also, they were generally unsuitable in situations where it was desirable, or mandatory, that the coating could be removed by chemical means, with common non-toxic solvents. It was generally known that monounsaturated acrylate monomers, especially those designed for use in contact with the human body, are difficult or impossible to cure by light using common polymerization-initiating systems, except in blends containing high percentage of di- or polyunsaturated monomers. However, the presence of monounsaturated acrylates at high concentrations is critical in situations when such coatings are intended to be used over, and to adhere to polymers such as acrylics, polystyrene, and polycarbonates. Polyunsaturated acrylic and methacrylic resins have poor characteristics as solvents and, therefore, are unable to effectively bond to the surfaces of polymers, which remain unaffected when exposed to such resins. However, lower ($C_1$–$C_4$) alkyl acrylates and methacrylates possess the ability to soften the surfaces of such polymers, which represents a necessary requirement to allow for effective bonding to them. Consequently, most commercially known acrylate coatings, particularly those used over acrylate polymers in dentistry, are based on such monomers.

Low reactivity of such monomers when cured by light is the reason why they were employed, almost exclusively, in self-cured systems. In light cured formulations of the prior art which contain monounsaturated acrylates, particularly those containing lower alkyl methacrylates, such monomers are present in blends containing, as major ingredients, acrylate monomers having, two or more unsaturated groups per molecule. Their presence was considered necessary to provide an adequate level of reactivity to such blends and, therefore, to assure a desirably short curing time.

It was generally recognized by those skilled in the art that in formulations developed for dental purposes, the polyunsaturated acrylates must represent more than 50% of the blend to achieve an acceptable curing time when using light-emitting dental curing instruments. However, such a high concentration of polyunsaturated monomers impairs the ability of the coating to bond to plastic surfaces and causes excessive brittleness of the coating, resulting from a high cross-linking density in the polymer. Also, a high concentration of polyunsaturated monomers causes a tendency toward crazing and the formation of an undesirable unpolymerized oxygen-inhibited layer on the surface of the cured material. The result is a surface lacking in smoothness, requiring time-consuming cleaning and finishing after cure, and susceptible to damage when impacted by hard objects.

SUMMARY OF THE INVENTION

The present invention provides improved adhesive coatings designed primarily for protecting, restoring, repairing, or modifying surfaces of, objects made of polymeric materials. Such improved adhesive coatings are particularly useful in application over worn, cracked, discolored, or otherwise defective objects made of polyacrylic, polystyrene, and polycarbonate resins. The adhesives of this invention are basically comprised of blends containing a substantial concentration of tetrahydrofurfuryl methacrylate and/or furfuryl methacrylate.

Formulations of this invention allow for making coatings featuring excellent adhesive properties and a low level of toxicity. Another important feature of such coatings is that they allow the formulator to control their hardness, flexibility, color-fastness, and solubility in organic solvents. Another important characteristic of formulations of this invention is that they eliminate the necessity for the use of toxic monomers, the presence of which was considered necessary, according to prior art, in order to assure an acceptable level of adhesion to polycarbonate, polyacrylate, and polystyrene resins. This feature is of particular importance in the field of dental/medical devices, especially those designed for intraoral use.

The coatings of this invention can be formulated in clear or tinted form. Acrylate or methacrylate monomers which cross-link and which are compatible with furfuryl and/or tetrahydrofurfuryl methacrylate, UV absorbers, antioxidants, pigments, dyes, fillers, extenders, and other additives may be included in the coating formulations in order to achieve desirable characteristics, such as resistance to specific chemical environments, light-fastness, aesthetics, rheological properties, hardness, shelf-life, increased or decreased adhesion to certain substrates, among others. These may be included in ranges of 5%–60% by weight of the total composition. Further, fillers may be selected from inorganic fillers selected from quartz, silica glass, aluminum oxide, zirconium silicate, and zirconium oxide and may comprise of up to 50% of the weight of the composition.

The present invention utilizes monomers which have been found to achieve the desirable physical and chemical characteristics of light-curable coatings which are superior over the prior art products in handling and performance, as well as their biological and environmental characteristics. Monounsaturated monomers—tetrahydrofurfuryl methacrylate and furfuryl methacrylate—were found to be able to be effectively cured by commercially available lights, operating in the visible wavelength range of 400 to 550 nanometers, in a time frame of less than ten minutes.

Also, other important advantages were realized from the use of these monomers. Unlike commonly used lower alkyl methacrylates, tetrahydrofurfuryl and furfuryl methacrylates are free of a pungent irritating odor, their toxicity to the skin is relatively low, and they pose little or no danger of developing chronic sensitization upon prolonged or repeated exposure. Their vapor pressure at moderate ambient temperatures is lower than those of lower alkyl methacrylates and, with minimum precautionary measures, they pose no danger of poisoning through the respiratory tract or through oral routes. They possess the ability to strongly bond to plastic materials, including polystyrene, polyalkylmethacrylates, and polycarbonates. The flexibility and hardness of the coating containing these monomers may be easily controlled by blending with di-or polyacrylate resins, such as trimethylopropane trimethacrylate, ethylene glycol dimethacrylate, diethylene glycol dimethacrylate, triethylene glycol dimethacrylate, etc., $C_3$–$C_6$ alkyl glycol dimethacrylates, and similar di-, tri-, and polymethacrylates.

Coatings composed primarily of tetrahydrofurfuryl methacrylate and furfuryl methacrylate, and their blends with other monounsaturated acrylates, are soluble in some common solvents, including acetone, chlorinated hydrocarbons, and methyl-ethyl ketone, making them especially suitable for applications where easy removal represents a desirable or critical feature. Such applications may include temporary protective coatings for electronic, optical, and other high-precision industries, as well as for the protection of brittle, fragile, or damage-susceptible items.

A discipline in which the easy removal of temporary or semi-permanent coatings is or may become of particular importance is dentistry, where they can be used for the temporary protection of tooth enamel against decalcification during orthodontic treatment, for the temporary enhancement of the esthetic appearance of teeth, for enhancing adhesion to dental polymers and plastic orthodontic appliances, and for repairing, restoring, or improving dental devices and prostheses made of acrylate resins, such as dentures, orthodontic plates and retainers, and acrylic teeth, and the like.

DETAILED DESCRIPTION OF THE PREFERRED EMBODIMENTS

In the preferred embodiment of this invention, the formulations of the adhesive coating are composed of:

(1) 40 to 99% of tetrahydrofurfuryl methacrylate, furfuryl methacrylate, or a mixture thereof; and (2) light-induced polymerization activators suitable for use for in light curable compositions. Such activators may include combinations of $\alpha,\beta$-diketones and tertiary aromatic amines exemplified by benzil, camphoroquinone, trialkylamines, and methacrylic acid esters of hydroxyalkyldialkylamines. Other commercially available initiators designed for light-curing acrylate resins are also applicable in compositions of this invention.

Optionally, such compositions may also include:

di-, tri-, or tetra-acrylate or methacrylate monomers; the presence of such monomers will result in increased hardness and better chemical resistance of the coatings and may accelerate the curing process. The concentration of such monomers in the preferred embodiment of this invention should not exceed 60%.

pigments or dyes.

stabilizers for enhancing the storage stability of the formulations, such as hydroquinone, methoxyhydroquinone and tert-butylohydroxytoluene (BHT).

antibacterial or antifungal agents.

therapeutic agents; the presence of sodium fluoride, stannous fluoride, and/or sodium monofluorophosphate is particularly desired in certain dental applications.

UV absorbers for the prevention of discoloration of the coatings upon exposure to UV and near-UV radiation.

Additives to control consistency, surface tension, etc. of the formulations in their uncured form.

EXAMPLES OF FORMULATIONS AND PROPERTIES OF THE ADHESIVE COATINGS OF THIS INVENTION

The invention is illustrated by the following examples, which are given here only for the purpose of a better understanding of the nature of the invention. They are presented, however, with no intention of fully encompassing its range and scope.

Example 1

The adhesive coating composition comprised:

| | |
|---|---|
| tetrahydrofurfuryl methacrylate | 98.9% |
| hydroxyethylodimethylamine | 0.75% |
| camphoroquinone | 0.35% |

The material was irradiated using two 150 watts light bulbs at a distance of 15 cm. The sample hard-cured in four minutes leaving no oxygen-inhibited layer of unpolymerized monomer on the surface. The Barcol Hardness of the cured material was 76. The resulting polymer may be dissolved in, or softened when exposed to, selected solvents or their mixtures, including acetone, methyl-ethyl ketone, methylene chloride, alkyl acetates, and lower alkyl acrylate esters.

Example 2

The adhesive coating composition comprised:

| | |
|---|---|
| tetrahydrofurfuryl methacrylate | 95.0% |
| ethylene glycol dimethacrylate | 3.0% |
| methacryloylethyl-diethylamine | 1.4% |
| camphoroquinone | 0.6% |

This composition cured under the conditions described in Example 1, producing a polymer free of an oxygen-inhibited layer and having Barcol Hardness of 80 in 3.5 minutes. The material was susceptible to slight surface softening upon five minutes exposure to acetone and methylethylketone.

Example 3

The adhesive coating composition comprised:

| | |
|---|---|
| furfuryl methacrylate | 89.0% |
| diurethane dimethacrylate | 10.0% |
| diethylaminoethyl methacrylate | 0.7% |
| camphoroquinone | 0.3% |

This blend cured in 4.5 minutes, leaving a thin oxygen-inhibited layer of partially unpolymerized material on the surface. The Barcol hardness of the cured polymer after removal of the unpolymerized layer was 80. The polymer exhibited superior chemical resistance to solvents when compared with formulations which are not cross linked.

What is claimed is:

1. A light-curable, dental sealant, varnish or glaze coating composition, comprising:

(a) 40 to 99% of the total composition of a cross-linking monomer selected from the group consisting of tetrahydrofurfuryl methacrylate, furfuryl methacrylate, and blends thereof; and (b) at least one polymerization initiating additive able to initiate the curing process upon exposure to light having a wavelength of 400 to 550 nanometers.

2. The composition of claim 1, comprising 5 to 60% of a cross-linking monomer comprised of a methacrylate compound or an acrylate compound or a combination thereof having at least two ethylenically unsaturated bonds per molecule.

3. The composition of claim 1, comprising up to 50% of inorganic filler selected from the group consisting of quartz, silica glass, aluminum oxide, zirconium silicate, and zirconium oxide.

4. The composition of claim 1, comprising up to 30% of polymeric fillers selected from the group consisting of polyamides, polyalkylenes, polyacrylics, polycarbonates, and polysilicones.

5. The composition of claim 1, comprising light-induced polymerization initiating additives comprised of $\alpha,\beta$-diketones and tertiary amines.

6. The composition of claim 5, wherein the $\alpha,\beta$-diketones are selected from the group consisting of camphoroquinone, benzil, and mixtures thereof.

* * * * *